United States Patent [19]

Suda et al.

[11] 3,969,420

[45] July 13, 1976

[54] PROCESS FOR RECOVERING RESORCINOL AND HYDROQUINONE IN MIXTURE

[75] Inventors: Hideaki Suda, Takaishi; Iwao Dohgane, Nishinomiya; Takashi Chinuki, Toyonaka; Kenji Tanimoto; Hirokazu Hosaka, both of Minoo; Yukimichi Nakao, Kobe; Yuji Ueda, Izumiotsu; Seiya Imada, Sakai; Hideki Yanagihara, Toyonaka; Kunihiko Tanaka, Ibaragi, all of Japan

[73] Assignee: Sumitomo Chemical Company, Limited, Osaka, Japan

[22] Filed: July 2, 1973

[21] Appl. No.: 375,920

[30] Foreign Application Priority Data

July 5, 1972   Japan................................ 47-67840

[52] U.S. Cl............................................ 260/621 A
[51] Int. Cl............................................. C07c 37/24
[58] Field of Search......... 260/621 A, 621 B, 621 C

[56] References Cited
UNITED STATES PATENTS

| | | | |
|---|---|---|---|
| 2,736,753 | 2/1956 | Jacobs............................ | 260/621 A |
| 2,748,172 | 5/1956 | Rodgers......................... | 260/621 C |

*Primary Examiner*—Bernard Helfin
*Assistant Examiner*—Norman Morgenstern
*Attorney, Agent, or Firm*—Stevens, Davis, Miller & Mosher

[57] ABSTRACT

Resorcinol and hydroquinone are recovered in mixture at a high purity from a solution containing resorcinol and hydroquinone, especially, a solution resulting from cleavage of oxidation products of isopropylbenzene and successive distillation of the cleavage product thereby to remove lower and higher boiling components therefrom, by adding 0.5 to 20 parts by weight of at least one solvent selected from aromatic hydrocarbons, aromatic hydrocarbons having lower alkyl substituent groups, and aliphatic hydrocarbons having 7 to 10 carbon atoms to one part by weight of said solution, if necessary, together with 1 to 30% by weight of at least one compound selected from ketones having 3 to 10 carbon atoms, alcohols having 1 to 5 carbon atoms and aliphatic esters having 3 to 5 carbon atoms, based on the weight of the organic solvent, dissolving the solution into the organic solvent by heating, separating a mixture of resorcinol and hydroquinone as a solid phase from the organic solvent layer after slow cooling, and recovering the solid phase as a product. The resorcinol and hydroquinone in the organic solvent layer are further recovered through extraction with water. When water is used together with the organic solvent from the beginning of extraction, the resorcinol and hydrocarbon are obtained in an aqueous layer.

9 Claims, No Drawings

PROCESS FOR RECOVERING RESORCINOL AND HYDROQUINONE IN MIXTURE

This invention relates to a process for recovering resorcinol and hydroquinone in mixture efficiently from a solution containing resorcinol and hydroquinone, particularly a solution resulting from cleavage of oxidation products of diisopropylbenzene with an acidic catalyst.

Diisopropylbenzene is oxidized in liquid phase with oxygen or oxygen-containing gas to give oxidation products containing diisopropylbenzene hydroperoxides, and the oxidation products containing diisopropylbenzene hydroperoxides are cleaved with an acidic catalyst to obtain resorcinol and hydroquinone.

However, a product solution resulting from the cleavage of the oxidation products containing diisopropylbenzene hydroperoxides with the acidic catalyst is a mixture consisting of acetone, water, unreacted diisopropylbenzene, phenol, isopropylphenol (which will be hereinafter referred to as IPP), isopropenylphenol (which will be hereinafter referred to as OST), hydroxyphenyldimethylcarbinol (which will be hereinafter referred to as OCA), acetylphenol (which will be hereinafter referred to as OAO), resorcinol, hydroquinone, their addition compounds, and other compounds boiling at a temperature much higher than the boiling points of resorcinol and hydroquinone.

When resorcinol and hydroquinone are to be recovered in mixture from said product solution, the lower boiling components such as acetone and water, and the higher boiling components than resorcinol and hydroquinone, that is, the so-called tars, can be relatively easily separated from the product solution by distillation. However, resorcinol and hydroquinone are not easily recovered from the resulting solution, though resorcinol and hydroquinone can be presumed separable therefrom by distillation based on a difference in boiling points. The separation by distillation has, however, several disadvantages as described below:

Firstly, resorcinol and hydroquinone are readily decomposed by heat.

Secondly, resorcinol and hydroquinone react with OST to form tarry addition products. Formation or decomposition of the tarry addition products depend upon heating temperature and thus the distillation is considerably influenced by the behaviors of the tarry addition products. It is known to azeotropically distill resorcinol and hydroquinone together with a special solvent, but recovery of the solvent is a serious problem in the industrial scale operation, and the azeotropic distillation has not yet completely solved the formation of the tarry addition products. The formation and decomposition of the addition products complicate operations of distillation process, and make the scale of distillation larger.

Thirdly, resorcinol and hydroquinone behave unfavourably, during the distillation operation through solidification, clogging, sublimation, etc., and thus the industrial scale recovery of resorcinol and hydroquinone by distillation is very difficult in their handling as well as operation, and therefore is industrially disadvantageous.

As a result of studies on a process for recovering resorcinol and hydroquinone in mixture at a temperature as low as possible, the present inventors have found a process for purifying and separating resorcinol and hydroquinone in mixture in high yield with a specific solvent from the solution containing resorcinol and hydroquinone.

The present invention is to provide a process for recovering resorcinol and hydroquinone in mixture from a solution resulting from cleavage of oxidation products of diisopropylbenzene with an acidic catalyst and successive distillation of the cleavage products to remove lower and higher boiling components, which comprises treating the solution with at least one organic solvent selected from the group consisting of aromatic hydrocarbons, aromatic hydrocarbons having at least one lower alkyl substituent, and aliphatic hydrocarbons, or with a mixture of at least one organic solvent defined above and water.

According to the present invention, 0.5 to 20 parts by weight of at least one organic solvent selected from aromatic hydrocarbons, which may have at least one lower alkyl substituent group, such as benzene, toluene, xylene, isopropyltoluene, diisopropylbenzene, triisopropylbenzene, etc., and aliphatic hydrocarbons having 7 to 10 carbon atoms, such as n-heptane and isoctane are added to one part by weight of a solution containing resorcinol and hydroquinone, obtained by cleaving an oxidation product solution of diisopropylbenzene by an acidic catalyst and removing lower boiling and higher boiling components by distillation from the solution resulting from the cleavage (the solution containing resorcinol and hydroquinone will be hereinafter referred to as "solution resulting from cleavage and distillation"), and the resulting mixture is subjected to heating and cooling in a range of from 150° to 0°C, preferably 120° to 20°C, whereby a solid portion and a liquid portion are obtained. More concretely speaking, the mixture of the solution resulting from cleavage and distillation with the solvent is heated up to about 150°C, preferably about 120°C, to completely dissolve a solid, while being stirred according to the conventional manner, and is thereafter cooled to about 0° to 20°C. Preferably, the cooling is conducted gradually in order to obtain crystals having a particle size as large as possible, whereby the subsequent filtration procedure can be facilitated, and the purity of resorcinol and hydroquinone in mixture can be improved.

The resulting solid portion contains 95 to 99% by weight of resorcinol and hydroquinone in mixture. The content of the mixture of resorcinol and hydroquinone in the solid portion can be further increased by repetition of the above procedure.

The present inventors have further found that a considerable effect can be attained against sticking of reaction products to a vessel wall or decrease in the resorcinol and hydroquinone content due to contamination of the solid portion by tarry materials during said procedure by adding 1 to 30% by weight of at least one compound selected from ketones having 3 to 10 carbon atoms, alcohols having 1 to 5 carbon atoms and aliphatic esters having 3 to 5 carbon atoms thereto, based on the weight of the organic solvent used in said procedure. Examples of the ketone include acetone, methyl ethyl ketone, methyl isobutyl ketone, diisopropyl ketone and methyl isopropyl ketone; examples of the alcohol include methanol, ethanol, isopropanol and tert-butanol; and examples of the ester include methyl acetate and ethyl acetate. That is, a mixture of resorcinol and hydroquinone having a purity of 99.8% or more can be recovered from the solution resulting from cleavage and distillation at percent recoveries of resorcinol and hydroquinone of 80 ± 5% and 90 to 95%, respectively, by adding said compound to said organic solvent as enumerated effective in the present invention.

Furthermore, the present inventors have found that resorcinol and hydroquinone contained in the liquid portion, that is, the organic solvent layer, can be extracted and recovered with 0.1 to 5 parts by weight of water per one part by weight of the organic solvent layer at 0° to 100°C, preferably 20° to 50°C, at a percent recovery of resorcinol and hydroquinone of each 99% or more, based on the weights of the resorcinol and hydroquinone dissolved in the organic solvent layer.

It has been also found that resorcinol and hydroquinone can be recovered from the solution resulting from cleavage and distillation through extraction with a combination of the organic solvent and water from the beginning. In this procedure, the solvent containing the organic solvent and water is used in an amount of 0.5 to 20 parts by weight based on one part by weight of the solution resulting from cleavage and distillation. The proportion of the organic solvent to water can be selected appropriately from a range of 1 : 0.5 to 1 : 10. This procedure can be conducted at a temperature of 50° to 100°C, preferably 70° to 90°C. In that case, resorcinol and hydroquinone are transferred to aqueous layer, and can be separated by decantation of the organic solvent layer from the aqueous layer, and therefore the cooling as in the aforesaid organic solvent treatment is not required.

It is possible in the present invention either to treat the solution from cleavage and distillation only with the organic solvent to recover almost all of resorcinol and hydroquinone in mixture as a solid phase and extract and recover the resorcinol and hydroquinone remaining in the organic solvent layer with water, or to extract a mixture of resorcinol and hydroquinone as an aqueous solution with a combination of the organic solvent and water from the beginning. That is, more favorable procedure can be selected from these two, depending upon prevailing situation. That is, according to the present invention, a mixture of resorcinol and hydroquinone having a purity of substantially quantitatively 99.5% or more can be obtained by treating the solution resulting from cleavage and distillation with said specific organic solvent including said additional compound and recovering resorcinol and hydroquinone remaining in the organic solvent layer with water.

The present invention will be described in detail by way of examples which are only illustrative, but not limitative, where parts and % are by weight, unless otherwise especially indicated.

EXAMPLE 1

500 parts of toluene as an organic solvent are added to 193.10 parts of a mixture consisting of 0.79 parts of phenol, 1.76 parts of IPP, 28.11 part of OST, 2.02 parts of OAO, 49.33 parts of hydroquinone, 71.15 parts of resorcinol and 39.94 parts of addition products. The mixture is dissolved in toluene by elevating a temperature to 95°C, and the resulting solution is slowly cooled and filtered at 38°C. 116.70 parts of the resulting crystals as in a finely powdery state, and contains 0.09 parts of phenol, 0.15 parts of IPP, 2.50 parts of OST, 0.46 parts of OAO, 47.77 parts of hydroquinone, 57.65 parts of resorcinol and 2.44 parts of the addition products.

The resulting crystals are repulped again in 500 parts of toluene at room temperature, and the resulting cakes are separated and dried under a reduced pressure, whereby 101.40 parts of crystals is obtained. The crystals are a mixture consisting of 0.01 part of phenol, 0.05 parts of IPP, 0.11 part of OST, 0.28 parts of OAO, 45.76 parts of hydroquinone, 55.01 part of resorcinol and 0.18 parts of the addition products. Percent recoveries of hydroquinone and resorcinol are 46.84% and 81.03%, respectively.

On the other hand, the toluene solution as a filtrate contains 0.70 part of phenol, 1.61 part of IPP, 25.61 part of OST, 1.56 parts of OAO, 1.56 parts of hydroquinone, 13.5 parts of resorcinol and 37.50 parts of the addition products. 200 parts of water are added to the toluene solution, and the resulting mixture is stirred at 30°C for 30 minutes, and then the resulting solvent layer and aqueous layer are decanted from each other. The solvent layer is admixed again with 200 parts of water and subjected to the same operation as above, repeatedly.

The resulting aqueous layers are joined together, and the joined water layer contains 1.48 parts of hydroquinone, and 12.79 parts of resorcinol. Overall percent recoveries of hydroquinone and resorcinol are 99.8% and 99.0%, respectively.

EXAMPLE 2

300 parts of toluene and 30 parts of methylisobutylketone as organic solvent mixture are added to 161.50 parts of a mixture consisting of 0.72 parts of phenol, 0.80 parts of IPP, 12.76 parts of OST, 1.15 parts of OAO, 38.63 parts of hydroquinone, 72.34 parts of resorcinol and 35.10 parts of addition products, and the mixture is dissolved into the organic solvent mixture by elevating a temperature to 95°C, and the resulting solution is slowly cooled to 38°C over a period of 2.5 hours, and then filtered. The resulting crystals are dried under a reduced pressure, whereby 99.47 parts of a mixture consisting of 0.02 parts of phenol, 0.03 parts of OST, 37.20 parts of hydroquinone and 62.24 parts of resorcinol are obtained. Percent recoveries of hydroquinone and resorcinol are 96.30% and 86.04%, respectively.

The toluene solution containing a small amount of methylisobutylketone as the filtrate contains 0.70 parts of phenol, 0.80 parts of IPP, 12.73 parts of OST, 1.15 parts of OAO, 1.43 parts of hydroquinone, 10.10 parts of resorcinol and 35.10 parts of the addition products, and is treated with water as in Example 1, whereby hydroquinone and resorcinol are recovered almost quantitatively.

EXAMPLE 3

An oxidation product solution of diisopropylbenzene is cleaved with sulfuric acid, after unreacted diisopropylbenzene and almost all amount of diisopropylbenzene monohydroperoxide have been removed from the oxidation product solution. Then, lower boiling components such as acetone and water, and higher boiling components than resorcinol and hydroquinone are removed from the solution resulting from the cleavage. 800 parts of octane as an organic solvent are added to 177.32 parts of the resulting solution consisting of 0.68 parts of phenol, 1.63 parts of IPP, 28.05 parts of OST, 1.89 parts of OAO, 46.48 parts of hydroquinone, 65.33 parts of resorcinol and 35.26 parts of the addition products, and the solution is dissolved in the organic solvent by heating the mixture to 110°C, and then slowly cooled to 20°C, and filtered. 110.58 parts of the resulting crystals contain 0.07 parts of phenol, 0.19 parts of IPP, 2.10 parts of OST, 0.41 part of OAO, 45.11 part of hydroquinone, 55.24 parts of resorcinol and 2.46 parts of the addition products. Percent recoveries of hydroquinone and resorcinol are 97.05% and 84.56%, respectively.

On the other hand, the octane solution as the filtrate contains 0.61 part of phenol, 1.44 parts of IPP, 25.75 parts of OST, 1.48 parts of OAO, 1.37 parts of hydroquinone, 10.09 parts of resorcinol and 32.80 parts of the addition products, and is treated with water as in Example 1 whereby hydroquinone and resorcinol are recovered almost quantitatively.

EXAMPLE 4

200 parts of cymene and 600 parts of water are added to a mixture consisting of 0.71 part of phenol, 1.02 parts of IPP, 10.35 parts of OST, 2.05 parts of OAO, 52.93 parts of hydroquinone, 95.24 parts of resorcinol and 23.65 parts of addition products, and the resulting mixture is heated to 80°C, and kept at that temperature for 20 minutes with stirring. Then, the mixture is left standing for 5 minutes and decanted while keeping the temperature at 75° to 80°C, whereby 762.94 parts of aqueous layer and 214.09 parts of a solvent layer are obtained.

The aqueous layer contains 0.27 parts of phenol, 0.29 parts of OST, 0.96 parts of OAO, 52.68 parts of hydroquinone, 93.91 part of resorcinol and 5.71 part of the addition products. The solvent layer contains 0.44 parts of phenol, 1.02 parts of IPP, 10.06 parts of OST, 1.09 parts of OAO, 0.25 parts of hydroquinone, 1.33 parts of resorcinol and 18.14 parts of the addition products. Percent recoveries of hydroquinone and resorcinol are 99.53% and 98.60%, respectively.

EXAMPLE 5

200 parts of a mixture containing 0.7% phenol 0.7% IPP, 10.0% OST, 0.8% OAO, 26.9% hydroquinone, 50.4% resorcinol and 10.5% addition products, 360 parts of toluene and 40 parts of diisopropylketone are charged into a three-necked vessel having a capacity for 1000 parts, provided with a condenser, thermometer and stirrer. The charge is heated up to 110°C with stirring at 300 to 400 rpm. Then, the charge is cooled down to 30°C over a period of 150 minutes, and filtered. The resulting cakes are repulped and washed with 360 parts of toluene, and filtered. The resulting cakes are dried, whereby 128 parts of white crystals are obtained. The crystals contain 0.02% phenol, 0.12% OST, 40.30% hydroquinone, and 59.56% resorcinol. Percent recoveries of hydroquinone and resorcinol are 95.9% and 75.6%, respectively.

EXAMPLE 6

400 parts per hour of a solvent layer containing 0.3% phenol, 0.3% IPP, 4.40% OST, 0.35% OAO, 0.7% hydroquinone, 5.0% resorcinol and 4.7% addition products obtained in Example 5 are continuously charged into an extractor column from the bottom, the column consisting of an extraction section having three theoretical contacting stages and a capacity for 320 parts, and a upper and lower decantor sections, each having a capacity for 100 parts and being positioned above or below the extractor section, and communicated thereto, and 200 parts per hour of water is also continuously charged into the extractor column from the top. Extraction is carried out at 25° to 30°C, whereby a raffinate layer is obtained from the top of the extractor column at a rate of 375 parts per hour, and an extract water layer is obtained from the bottom of the extractor column at a rate of 225 parts per hour. Then, 225 parts of the water layer are contacted with 200 parts of isobutyl acetate at room temperature for 20 minutes with stirring to extract organic matters. The resulting isobutyl acetate layer is concentrated, whereby 24 parts of solid matters, which contain 1.0% phenol, 1.0% OST, 2.5% OAO, 11.0% hydroquinone, 78.5% resorcinol and 5.5% addition products. Extraction yields of hydroquinone and resorcinol are 94.3% and 94.2%, respectively.

Overall yields of hydroquinone and resorcinol by recrystallization and extraction recovery in the processes of Examples 5 and 6 are 99.7% and 98.5%, respectively, (exclusive of hydroquinone and resorcinol contained in repulping and washing toluene of Example 5).

Total crystal mixture of the recrystallized product and extraction-recovered product contains 0.03% phenol, 0.12% OST, 0.40% OAO, 35.80% hydroquinone, 62.78% resorcinol and 0.87% addition products.

What is claimed is:

1. A process for recovering resorcinol and hydroquinone in mixture from a solution resulting from the acid catalyzed cleavage of the resulting oxidation products of the liquid phase, oxygen or oxygen containing gas oxidation of diisopropylbenzene and successive distillation of the cleavage products to remove lower and higher boiling components, which comprises adding to said solution a mixed organic solvent of (1) at least one hydrocarbon solvent selected from the group consisting of alkanes having 7 to 10 carbon atoms, benzene and lower alkyl substituted benzene and (2) at least one compound selected from the group consisting of acetone, methylethylketone, methylisopropylketone, methylisobutylketone, methanol, ethanol, isopropanol, tert.-butanol, methyl acetate and ethyl acetate, dissolving the resulting mixture by heating, slowly cooling the resulting solution, thereby separating a solid phase containing resorcinol and hydroquinone and the organic solvent layer, and recovering the solid phase of the mixture of resorcinol and hydroquinone from the organic solvent layer.

2. A process according to claim 1, wherein the lower alkyl substituted benzene is toluene, xylene, isopropyltoluene, diisopropyltoluene or triisopropyltoluene.

3. A process according to claim 1, wherein 0.5 to 20 parts by weight of the mixed organic solvent are added to one part by weight of the solution.

4. A process according to claim 1, wherein the dissolution and slow cooling are carried out in a range of 150° to 0°C.

5. A process according to claim 1, wherein 1 to 30% by weight of the compound is used, based on the weight of the mixed organic solvent.

6. A process according to claim 1, wherein the mixed organic solvent phase after recovery of the resorcinol and hydroquinone solid phase is contacted with water, thereby to extract resorcinol and hydroquinone into the aqueous phase.

7. A process according to claim 6, wherein 0.1 to 5 parts by weight of water is used per one part by weight of the mixed organic solvent layer.

8. A process according to claim 6, wherein the water contact is carried out at 0° to 100°C.

9. The process according to claim 1, wherein the alkane is n-heptane or iso-octane.

* * * * *